United States Patent [19]  [11] 4,048,337
Fabbian  [45] Sept. 13, 1977

[54] GYPSUM DUST DILUENTS FOR USE IN PESTICIDES AND FERTILIZING PRODUCTS

[76] Inventor: Bruno Fabbian, Via XI Febbraio, 27 Asigliano Veneto (Vicenza), Italy

[21] Appl. No.: 624,573

[22] Filed: Oct. 21, 1975

Related U.S. Application Data

[63] Continuation-in-part of Ser. No. 495,330, Aug. 7, 1974, abandoned.

[30] Foreign Application Priority Data

Aug. 24, 1973 Italy ................................. 85592/73

[51] Int. Cl.$^2$ ............................................. A01N 9/00
[52] U.S. Cl. ................................ 424/357; 71/DIG. 1; 424/78
[58] Field of Search ....................... 424/154, 357, 781

[56] References Cited

U.S. PATENT DOCUMENTS

| | | | |
|---|---|---|---|
| 3,062,637 | 11/1962 | Marples et al. | 424/357 |
| 3,553,321 | 1/1971 | Zilli et al. | 424/357 |
| 3,832,468 | 8/1974 | Hyson et al. | 424/357 |

OTHER PUBLICATIONS

Abstract of Japanese Pat. No. 46-20518 (1971).
Abstract of Japanese Pat. No. 47-1798 (1972).

*Primary Examiner*—V. D. Turner
*Attorney, Agent, or Firm*—Bucknam and Archer

[57] ABSTRACT

Dust diluents and carriers of the gypsum series are prepared in granular or powder form, with absorbing properties, for use in pesticides and leaf and soil fertilizing products, from minerals of the gypsum series, particularly hydrated sulphates of selenite, sericulite, alabaster or anhydrous sulphate form, or the anhydrite form. The calcium sulfate is baked in order to produce baked, Alpha, Beta, or hydraulic chalk, according to the baking temperature; it is deactivated and water is added to form a dispersion which is allowed to settle. A substance is added which may be a salt of an alkaline or alkaline-earth metal, or double aluminum and potassium sulphate, a source of electrons, an oxygen or nitrogen donor, a non-ionic, anionic, cationic surface active agent or mixtures thereof, a vegetable polymer, a polymerized vegetable gum, a polymerized vegetable oil, polyvinyl chloride or acetate in natural condition or emulsified, a specific setting retarder, a tannic derivative, a ligninsulphite or a ligninsulphonate of alkaline or earth-alkaline metal or of an amphoteric metal, or a specific synthetic plasticizing product for plastic or polymerizable materials or for rubber mixtures. The products have little or no acidic centers, no surface catalytic activity nor cationic exchange capacity.

3 Claims, No Drawings

GYPSUM DUST DILUENTS FOR USE IN PESTICIDES AND FERTILIZING PRODUCTS

This application is a continuation-in-part of application Ser. No. 495,330, filed Aug. 7, 1974, now abandoned.

The present invention relates to novel compositions to be used particularly as pesticides and as agents for the protection of agricultural products. The invention also relates to the method of preparation of the novel compositions of the invention.

In order to distribute an agent to protect crops and/or assist in their growth, the agent must be in such a form and of such concentration that it can promote biological efficiency and must be capable of being applied to the soil.

Up to the present time, the most frequently used forms have been wettable powders; dusts; emulsifiable concentrates; emulsions which can be diluted in water; solutions which can be mixed with water; granular formulations; and pellets.

These forms comprise the following: A toxicant or active ingredient which may be a natural or synthetic product in a medium of high degree of purity; surface active agents, adhesives, colouring, sinergysing, stabilizing elements, as well as regulating elements for evaporation and emission; and inert ingredients (aromatic, aliphatic, polar and water solvents, solid mineral, or synthetic or vegetable materials). Here the word 'inert' is not used in the absolute sense but to indicate passivity with respect to the compositions and to the action of the other ingredients of the agent. These inert ingredients are used to bring the concentration of active ingredients to within the desired or authorized limits. The following are widely used: As wettable or dust pesticide powders, there are used talc, kaolonites, diatomites, silicon dioxides or silica, carbonates of alkaline-earth metals, alkaline earth metal hydroxides, montmorrillonites, attapulgites, vegetal products, tripolites, dolomites, clay products, phosphates, pyrophyllites, synthetic and other products. As granular or granulated products, there are used vegetable products, calcites, diatomites, dolomites, vermiculites, sulphates, mica, pyrophilites, montmorrillonites, kaolinites, attapulgites, clays, phosphates, nitrates, sulphates, silicates, pumices, synthetic and other products.

Obviously, as additives and carriers the products should not interact at all with the active ingredients nor with the additives of each composition. Therefore, for every formulation it is necessary to determine the mineralogic, structural, chemical and physical characteristics of the inert ingredients.

Some of these characteristics may have the undesirable effect of inducing and catalyzing the decomposition of the active component, for instance they may effect:

a. The water content (constitutional, combination or elaboration residual water);
b. Surface acidic centres or surface catalytic activity;
c. Cationic exchange capacity; depending upon its mineralogical group, the crystallographic structure, and the working process.

In spite of long studies, the disadvantages specified herein, particularly under (b) and (c), have not yet been totally eliminated, but it has been possible to reduce the disadvantages by means of such substances as, for instance: (a) Glycols; Urea; Hexamethylenetetramine to be introduced during production.

Unfortunately it is not always possible, for technical and cost reasons to introduce these agents into the formulations.

Furthermore, in addition to being a main contributory cause of the degration of the active ingredients, the catalytic surface activity and the ionic exchange capacity may, in some cases, immediately and definitively effect changes in the chemical structure of the active agents to the point of totally destroying their biological efficiency.

The object of the present invention is to make compositions in which the carrier does not affect the activity of the active component.

Another object is to make carriers from inert substances free, or essentially free, from acidic centers with little or negligible exchange capacity.

Studies and practical trials, performed with certain minerals have yielded inert products totally free from acidic centers, or with only light traces of acidic centers in which ionic exchange capacity is so reduced as to be negligible so that the stability of the active principles is not affected. These minerals include the following: Selenites, sericolites, alabaster, anhydrites, aragonites, apatites, chalk stones, limestones, saccharoid marbles, lime building stones, dolomitic limestones, marl or loam rock limestones, white clays, calcareous tufas, stalactites, stalagmites, baritines, to which there are added substances including alkaline metal inorganic salts, alkaline-earth metal inorganic salts, different combinations of non-ionic, anionic and cationic surface active agents, glycols, urea, hexamethylenetetramine.

Among the beforementioned minerals, those of the "gypsum series", have proved to be particularly suitable and their characteristics are given below:

| MINERALOGIC GROUP | |
|---|---|
| 6th Class minerals - Gypsum series | |
| Hydrated sulphates, exempt from foreign anions in the forms: | |
| Crystalline | = Selenite |
| Fibrous | = Sericulite |
| Compact, spathic, saccharoid | = Alabaster |
| Chemical name | = dihydrate calcium sulphate |
| Chemical formula | = $CaSO_4 . 2 H_2O$ |
| Class | = Prismatic |
| Crystallization system | = Monoclinic |
| Reticle | = Ionic |
| Hardness (Mohs scale) | = 2 (two) |
| Specific weight | = 2.30 |
| Calcium anhydrous sulphate in the form: | |
| Crystalline | = Anhydrite |
| Chemical name | = Anhydrous calcium sulphate |
| Chemical formula | = $CaSO_4$ |
| Class | = Bypyramidic |
| Crystallization system | = Rhombic |
| Reticle | = Ionic |
| Hardness (Mohs Scale) | = 3 - 3.5 |
| Specific weight | = 3.0 |

According to colloidal theories, the "settling" phenomenon of these materials seems to be due to the action of water after baking has occurred, because gels are built from the solution or dispersion of colloidal nature of calcium sulfate dihydrate. From the gels crystals of calcium sulfate dihydrate are formed as long needles which are thickly disposed and closely interwoven, so that hardening and greater cohesion among the crystals themselves is achieved.

According to the present invention there are provided dust diluents and carriers of the gypsum series and a method of producing the same. The method comprises the following steps:

BAKING

In order to transform $CaSO_4 \cdot 2H_2O$ into a more useful product within the scope of the present invention, the material is baked so that the baking temperature is gradually increased whereby the following products result:

| | |
|---|---|
| $CaSO_4 \cdot 2H_2O$ (120 – 130° C) $CaSO_4 \frac{1}{2} H_2O$ | Baked chalk |
| $CaSO_4 \frac{1}{2} H_2O$ (over 130° C) $CaSO_4$ | Alpha chalk |
| $CaSO_4$ . Alpha (over 300° C) $CaSO_4 \beta$ | Beta chalk |
| $CaSO_4$ . Beta (over 600° C) $CaSO_4 \gamma$ | Gamma chalk |
| $CaSO_4$ . Gamma (800 – 1,000° C) | (A variety of the anhydrite) Hydraulic chalk |

DEACTIVATING AND "SETTING"

The alpha chalk, has empty spaces in its reticle and may be easily dissolved in water. The addition under stirring to the baked chalk, alpha chalk, beta chalk, gamma chalk or anhydrite, hydraulic chalk or their mixtures, of water, in appropriate proportions and inorganic salts of alkaline and alkaline-earth metals, double aluminum and potassium sulphates, of substances which are a source of electrons, oxygen and nitrogen donors (glycols, hexamethylenetetramine, urea and others) of combinations of special particular non-ionic, anionic and cationic surface-active agents, of natural and/or synthetic resins, of polymers of vegetable origin, polymerized vegetable gums, polymerized vegetable oils, polyvinyl chlorides or acetates, unchanged or emulsified, specific setting retarders, tannic derivatives, or ligninsulphites or ligninsulphonates of alkaline or alkaline earth or amphoteric metals, specific synthetic plasticizers for plastic of polymerizable materials or for mixtures of rubber, . . . in suitable proportions have yielded some products with a powdery or granular form and particularly suitable for use in pesticides and other agents for protecting agricultural products. The polymerized vegetable gums may be gum arabic, gum trapacanth colophony. Setting retarders may be for instance citric acid, acetic acid, boric acid, lactic acid, calcium alginate.

The term "tannic derivatives" is used to designate derivatives of tannic acid, tannin and salts of tannic acid.

The term "polymerized vegetable oils" is used to designate for instance crude and aerated linseed oil, castor oil and soya bean oil.

The term "synthetic plasticizers" is used to designate substances such as butyl or isobutyl phthalate, butyl or isobutyl maleate.

The term "glycols" is used herein to designate monoethylene glycol, diethylene glycol, triethylene glycol, propylene glycol, polypropylene glycol.

The additive may be, for instance, sodium bisulfate monohydrate, acetic acid, carboxymethylcellulose, polyvinyl acetate, polyoxyethylene sorbitol oleate.

Conventional industrial processes may be used for the baking, granulation, screening, pelletizing and drying of materials (or mixtures thereof with phytoiathric substances) and for the grinding of the inert products.

The inert products according to the present invention may be of granular or powdered form.

The inert products according to the present invention and having a granular form have the following chemical and physical characteristics:

Physical condition—Granular with globular shaped particles.
Colour—From white to light tonalities of brown or grey.
Homogeneity—of colour: excellent; or size: variable granulometric extension or distribution, according to the requirements and the specific use whereto the product may be destined.
pH. Suspension at the 5%—Between 6.0 and 9.0 (according to to the necessity or requirements).
Fluidity—Good, such that it will not produce agglomeration or packing phenomena.
Moisture—From 0.50% up to a maximum of 3.00% understood as such, that is only the residual water, not the water of formation, crystallization, or chemically bound water. This residual water may be extracted as an azeotropic mixture with xylene and/or benzene, by means of the Dean & Stark device, modified by Marcusson.
Hygroscopicity—From 0.3% up to a maximum of 5%.
Hardness or tendency to chip—Enough to maintain unchanged the granules shape (with possible light modifications of the granulometric distribution) during the processing and the corresponding packaging operations, storage, transportation and distribution, by means of mechanical devices on the ground or in the air.
Maximum oil-absorption—from 14 up to 26G of oil for 100G of granular product. White mineral oil used, having a viscosity of 2.8°–3.0° E at 100° F (37.8° C).
Acidic centres or surface catalytic activity—Either absent or in light traces. (Qualitative test with indicator p-dimethylaminoazobenzene).
Cation exchange capacity—From Zero to 3 me/g 100 of granular (Qualitative test with benzylamine and n-butylamine).
Density—Up to about 1.0 g/ml: packed from about 0.7 to 1.2 g/ml,
Particle size—From 3.00 mm to 10.00 mm; From 1.50 mm to 3.00 mm; From 0.75 mm to 2.00 mm; From 0.35 mm to 0.75 mm; From 0.15 mm to 0.25 mm; according to necessities and requirements.

Inert products according to the present invention and taking the form of a dry powder have the following chemical and physical characteristics:

Physical condition—powder
Colour—from white to light tonalities of brown or grey.
Homogeneity—excellent.
pH. Suspension at 5%—from 6.0 to 9.0 (according to necessities and requirements).
Density—from 0.4 to 0.6 g/ml (approximately) after settling or bedding. From 0.5 to 0.8 g/ml (approximately).
Fluidity—moderate
Moisture—from 0.5% to a maximum of 3%.
Hygroscopicity—from 0.3% to a maximum of 5%.
Maximum oil absorption—from 14 to 20 G of oil for 100G of product.
Acidic centres or surface catalytic activity—either absent or in light traces. (Qualitative test with p-dimethylaminoazobenzene).

Cation exchange capacity—from Zero to 3 me/G 100 of product (quantitative test with benzylamine and n-butylamine).

Particle size—−90 micron, −74 micron, −53 micron, −44 micron, and possibly other sizes according to requirements.

All the mentioned ingredients gave to the finished powdered or granular products, and particularly the latter, a further positive characteristic i.e. a slower and more controlled erogation of the volatile pesticides by means of which the persistence of their biologicl efficiency is increased within acceptable limits, with negligible interference or increase in the residual substances of the active principles over the authorized limits.

All the finished products according to the present invention may be delivered in different colours, especially blue which allows a better identification of the products at the distribution stage.

For the preparation of the carrier according to the present invention, the substance which is added to the carrier is in an amount of 0.001–10%. The amount of water varies between 15 and 70% of the weight of the material. After the calcium sulfate has been baked, water and the additive are added. The material is ground, screened and stirred at a temperature between 30° and 300° C. The following examples illustrate the preparation of the carrier.

EXAMPLE 1

Baked chalk ($CaSO_4 \cdot 1/2H_2O$) is prepared by heting $CaSO_4 \cdot 2H_2O$ at 120°–130° C. A mixture is prepared from the following:

| | | |
|---|---|---|
| $CaSO_4 \cdot \frac{1}{2}H_2O$ | g | 1.000 |
| $H_2O$ | g | 450 |
| $NaHSO_4 \cdot H_2O$ | g | 1 |

The material is placed in a granulator for 8 minutes to give a granular composition of average particle size between 0.05 and 10 mm. After screening, the material is dried at 40°–50° C while the desired amount of water is reached.

EXAMPLE 2

| $CaSO_4 \frac{1}{2} H_2O$ | 175° C | $CaSO_4$ | alfa chalk |
|---|---|---|---|
| $CaSO_4$ alfa | | g | 1.000 |
| $H_2O$ | | g | 300 |
| $CH_3COOH$ | | g | 1.5 |

The material is granulated in a granulator for 15 minutes to give granules of average particle size 0.05–0.10 mm. After screening, the material is dried at 50°–60° C to achieve the desired water content.

EXAMPLE 3

| $CaSO_4$ alfa | 360° | $CaSO_4$ | beta chalk |
|---|---|---|---|
| $CaSO_4$ beta | | g | 1.000 |
| $H_2O$ | | g | 350 |
| CMC (carboxymethylcellulose) | | g | 1 |

The mixture is kept in the granulator for 10 minutes to give granules of average particle 0.05–0.10 mm. After screening, the material is dried at 40°–60° C until the desired degree of drying is reached.

EXAMPLE 4

| | | |
|---|---|---|
| $CaSO_4$ alfa | g | 300 |
| $CaSO_4$ beta | g | 700 |
| $H_2O$ | g | 300 + 450 |
| emulsion of polyvinyl acetate | g | 5 |

The mixture is kept in the granulator for 5 minutes until granules of average particle size 0.05–0.10 mm are formed. After screening, the mixture is dried at 40°–50° C until the desired degree of drying is reached.

EXAMPLE 5

| | | |
|---|---|---|
| $CaSO_4 \cdot \frac{1}{2}H_2O$ | g | 100 + 150 |
| $CaSO_4$ alfa | g | 150 + 350 |
| $CaSO_4$ beta | g | 750 + 500 |
| $H_2O$ | g | 300 + 450 |
| Polyoxyethylene sorbitol oleate (non-ionic emulsifier) | g | 0.5 |

The mixture is kept in the granulator for 12 minutes until granules of average particle size 0.05–0.10 mm are formed. After screening, the material is dried at 40°–60° C until the desired degree of moisture is achieved. The material is powder form is obtained by subsequently crushing the granulated material.

The proportion of the active pesticidal component to the carrier in granular or powdery form or both in the composition according to the present invention varies over a wide range and may be between 1:2 and 1:15 part by weight. Some examples of the pesticidal compositions which may be prepared with the granular or powdery calcium sulfate and additive are given hereinbelow for the purpose of illustration of the invention. In each case the additive is monobasic calcium phosphate or polyvinyl acetate.

| 6) | GRANULAR PARATHION | | |
|---|---|---|---|
| | 0,0-diethyl 0-p-nitrophenylphosphorothioate | g. | 10 |
| | granular; particle size in mm. 0.05 – 1.30 | g | 90 |
| 7) | GRANULAR DOWCO 179 | | |
| | Diethyl 3,5,6-trichloropyridylphosphorothioate | g | 5 + 8 |
| | epichlorohydrin | g | 1 + 2 |
| | granular; particle size in mm. 0.50 – 1.30 | g | 94 + 90 |
| 8) | GRANULAR DIAZINON | | |
| | Diethyl 2-isopropyl-6-methyl-4-pyrimidinyl phosphorothionate | g | 5 |
| | granular; particle size in mm. 0.50– 1.30 | g | 95 |
| 9) | GRANULAR PHORATE | | |
| | 0,0-diethyl S-(ethylthio)-methyl phosphorodithioate | g | 10 |
| | granular; particle size in mm. 0.50 – 1.30 | g | 90. |
| 10) | GRANULAR ORDRAM | | |
| | S-ethyl N,N-hexamethylenethiolocarbamate | g | 8 |
| | granular; particle size in mm. 1:30 – 2.50 | g | 92 |
| 11) | 2,4-D GRANULAR (that is the isopropyl ester of 2,4-dichlorophenoxy acetic acid | | |

| | -continued | | |
|---|---|---|---|
| | 2,4-D isopropyl ester | g | 16 |
| | granular; particle size in mm. 1.30 – 2.50 | g | 84 |
| 12) | PARATHION DUST | | |
| | 0,0-diethyl 0-p-nitrophenylphosphorthioate | g | 25 |
| | Silica colloidal | g | 15 |
| | inert powder 53 micron diameter | g | 60 |
| 13) | PARATHION: WETTABLE POWDER | | |
| | 0,0-diethyl 0-p-nitrophenylphosphorothioate | g | 25 |
| | Silica colloidal | g | 15 |
| | Surface active agents | g | 5 |
| | inert powder 44 micron | g | 55 |

The compositions of this invention are useful as agricultural products in the treatment of soil and are applied to the soil by methods known in the art.

What is claimed is:

1. A method of producing a dust diluent of carrier for pesticides from anhydrous or hydrated calcium sulfate, in granular or powder form, comprising the steps of baking a mineral consisting essentially of calcium sulfate at a temperature between 120°–130° C to produce baked chalk, at a temperature of 130°–300° C to produce alpha chalk, at a temperature between 300°–600° C to produce beta chalk, at a temperature between 600°–800° C to produce gamma chalk and at a temperature between 800°–1000° C to produce hydraulic chalk, adding water to disperse or dissolve at least one of said baked products and allowing settling to occur, adding a substance which is a double sulfate of aluminum and potassium, a non-ionic, an anionic or cationic surface active agent, carboxymethylcellulose, urea, a glycol, hexamethylene-tetramine, sodium bisulfate dihydrate, polyvinyl acetate, polyvinyl chloride, monobasic calcium phosphate, a polymerized vegetable adhesive, or a polymerized vegetable oil, drying, pellitizing or grinding so as to obtain a product in granular or powder form having essentially no acidic centers, no surface catalytic activity and no cationic exchange activity.

2. A diluent or carrier for incorporation in a pesticidal product containing a pesticidally active ingredient comprising crystals of calcium sulfate dihydrate and an additive in an amount effective to reduce the rate of decomposition of the pesticidally active ingredient, and additive being a double sulfate of aluminum and potassium, a non-ionic, anionic or cationic surface active agent, carboxymethylcellulose, urea, a glycol, hexamethylene-tetramine, sodium bisulfate dihydrate, polyvinyl acetate, polyvinyl chloride or monobasic calcium phosphate, said additive being in the amount of 0.001–10%, said diluent or carrier having 0.05–3% moisture, being of pH 6–9 and of hydroscopicity 0.3 up to 5%, essentially free of acidic centers and essentially free of surface activity.

3. A diluent or carrier for incorporation in pesticidal compositions containing a pesticidally active ingredient prepared by baking a calcium sulfate mineral at a temperature between 120°–1000° C to produce baked chalk, alpha chalk, beta chalk, gamma chalk or hydraulic chalk, adding water in amount between 15 and 70% of the weight of said baked calcium sulfate to form a dispersion, allowing settling to occur, adding 0.001–10% by weight of an additive, in an amount which is effective to reduce the rate of decomposition of the pesticidally active ingredient, said additive being a double sulfate of aluminum and potassium, a non-ionic, anionic or cationic surface active agent, carboxymethylcellullose, urea, a glycol, hexamethylene-tetramine, sodium bisulfate dihydrate, polyvinyl acetate, polyvinyl chloride or monobasic calcium phosphate, converting the material thus obtained to granular or powdery form and drying at 30°–300° C.

* * * * *